US011213695B2

(12) United States Patent
Fewkes et al.

(10) Patent No.: US 11,213,695 B2
(45) Date of Patent: Jan. 4, 2022

(54) ILLUMINATED BANDAGE AND METHOD FOR DISINFECTING A WOUND

(71) Applicant: Corning Incorporated, Corning, NY (US)

(72) Inventors: Edward John Fewkes, Corning, NY (US); Stephan Lvovich Logunov, Corning, NY (US); Cynthia Jean Wilson, Corning, NY (US)

(73) Assignee: Corning Incorporated, Corning, NY (US)

( * ) Notice: Subject to any disclaimer, the term of this patent is extended or adjusted under 35 U.S.C. 154(b) by 766 days.

(21) Appl. No.: 14/540,293

(22) Filed: Nov. 13, 2014

(65) Prior Publication Data

US 2015/0148734 A1  May 28, 2015

Related U.S. Application Data

(60) Provisional application No. 61/908,919, filed on Nov. 26, 2013.

(51) Int. Cl.
*A61N 5/06* (2006.01)
*A61F 13/00* (2006.01)
*A61L 2/10* (2006.01)

(52) U.S. Cl.
CPC ...... *A61N 5/0624* (2013.01); *A61F 13/00063* (2013.01); *A61L 2/10* (2013.01);
(Continued)

(58) Field of Classification Search
CPC ............... A61N 5/0624; A61N 5/0616; A61N 2005/063; A61N 2005/0645;
(Continued)

(56) References Cited

U.S. PATENT DOCUMENTS 4,234,907 A * 11/1980 Daniel ................. A41D 27/085
139/420 R
6,551,346 B2   4/2003 Crossley
(Continued)

FOREIGN PATENT DOCUMENTS

CN    104010710 A    8/2014
CN    204840698 U   12/2015
(Continued)

OTHER PUBLICATIONS

International Search Report, issued in connection with corresponding PCT application No. PCT/US2014/065618, dated Jan. 27, 2015.
(Continued)

*Primary Examiner* — Rex R Holmes
(74) *Attorney, Agent, or Firm* — Svetlana Z. Short; Payal Patel

(57) ABSTRACT

An illuminated bandage and method of disinfecting a wound. The illuminated bandage includes a power source, a light source coupled to the power source to generate light and a patch. The patch includes a supporting medium and at least one light diffusing element in the supporting medium and optically coupled to the light source. The light diffusing element outputs light to promote a photochemical reaction to disinfect a wound surface proximate thereto.

11 Claims, 2 Drawing Sheets

(52) U.S. Cl.
CPC ........ *A61N 5/0616* (2013.01); *A61L 2202/21* (2013.01); *A61N 2005/063* (2013.01); *A61N 2005/0645* (2013.01); *A61N 2005/0661* (2013.01)

(58) Field of Classification Search
CPC ....... A61N 2005/0661; A61F 13/00063; A61L 2/10; A61L 2202/21
See application file for complete search history.

(56) References Cited

U.S. PATENT DOCUMENTS

| | | | |
|---|---|---|---|
| 7,450,806 B2 | 11/2008 | Bookbinder et al. | |
| 7,505,660 B2 | 3/2009 | Bickham et al. | |
| 7,542,645 B1* | 6/2009 | Hua | G02B 6/02366 385/123 |
| 7,930,904 B2 | 4/2011 | Bookbinder et al. | |
| 8,404,273 B2 | 3/2013 | Baumgart et al. | |
| 8,585,681 B2 | 11/2013 | Boenig et al. | |
| 8,779,386 B2 | 7/2014 | Bak | |
| 8,980,174 B2 | 3/2015 | Haytman et al. | |
| 9,039,966 B2 | 5/2015 | Anderson et al. | |
| 9,067,059 B2 | 6/2015 | Bissig et al. | |
| 9,259,513 B2 | 2/2016 | Bedwell et al. | |
| 9,393,339 B2 | 7/2016 | Park et al. | |
| 9,439,989 B2 | 9/2016 | Lalicki et al. | |
| 9,550,005 B2 | 1/2017 | Lin et al. | |
| 9,795,466 B2 | 10/2017 | Piergallini et al. | |
| 9,808,647 B2 | 11/2017 | Rhodes et al. | |
| 9,925,390 B2 | 3/2018 | Yehezkel | |
| 9,943,379 B2 | 4/2018 | Gregg, II et al. | |
| 10,046,070 B1 | 8/2018 | Zaborsky et al. | |
| 10,166,402 B2 | 1/2019 | Brennan et al. | |
| 10,183,144 B2 | 1/2019 | Tang et al. | |
| 10,241,035 B2 | 3/2019 | Bonnick et al. | |
| 2006/0085052 A1 | 4/2006 | Feuerstein et al. | |
| 2006/0167532 A1* | 7/2006 | Parker | A61N 5/0616 607/88 |
| 2006/0206171 A1 | 9/2006 | Gertner et al. | |
| 2006/0257095 A1* | 11/2006 | Walt | A61B 5/6804 385/147 |
| 2007/0239232 A1* | 10/2007 | Kurtz | A61N 5/0613 607/87 |
| 2009/0257910 A1 | 10/2009 | Segal | |
| 2010/0268151 A1 | 10/2010 | Mauge et al. | |
| 2011/0122646 A1* | 5/2011 | Bickham | G02B 6/0003 362/554 |
| 2011/0305035 A1 | 12/2011 | Bickham et al. | |
| 2012/0191031 A1 | 7/2012 | Quisenberry | |
| 2012/0303101 A1* | 11/2012 | Rogers | A61N 5/062 607/90 |
| 2013/0035629 A1* | 2/2013 | Soltz | A61M 35/00 604/20 |
| 2015/0080709 A1 | 3/2015 | Chaturvedi | |
| 2018/0036443 A1 | 2/2018 | Messerly | |
| 2018/0147417 A1 | 5/2018 | Rantala | |
| 2018/0178031 A1 | 6/2018 | Wu | |
| 2018/0207302 A1 | 7/2018 | Vasilenko | |
| 2018/0304094 A1 | 10/2018 | Hicks et al. | |
| 2018/0326104 A1 | 11/2018 | Hawkins et al. | |

FOREIGN PATENT DOCUMENTS

| | | |
|---|---|---|
| CN | 106178280 A | 12/2016 |
| CN | 106178282 A | 12/2016 |
| CN | 105396169 B | 6/2018 |
| CN | 108671243 A | 10/2018 |
| EP | 2854944 A1 | 4/2015 |
| EP | 2701789 B1 | 5/2017 |
| JP | 2008-539808 A | 11/2008 |
| JP | 2013-511749 A | 4/2013 |
| JP | 05546575 B2 | 7/2014 |
| JP | 2014-524754 A | 9/2014 |
| KR | 1362704 B1 | 2/2014 |
| KR | 1851576 B1 | 4/2018 |
| KR | 2018049757 A | 5/2018 |
| KR | 1892996 B1 | 8/2018 |
| KR | 2018135256 A | 12/2018 |
| KR | 2018135257 A | 12/2018 |
| WO | 2007/106856 | 9/2007 |
| WO | 2010011299 | 1/2010 |
| WO | 2011063214 | 5/2011 |
| WO | 2012/149092 A1 | 11/2012 |
| WO | 2013/177674 A1 | 12/2013 |
| WO | 2015168129 A1 | 11/2015 |
| WO | 2018009864 A1 | 1/2018 |
| WO | 2019/027478 A1 | 2/2019 |
| WO | 2019025808 A1 | 2/2019 |

OTHER PUBLICATIONS

International Search Report and Written Opinion of the International Searching Authority; PCT/US14/65618; dated Jan. 27, 2015; 8 Pages; European Patent Office.

Japanese Patent Application No. 2016-532004 Decision to Grant a Patent dated Nov. 4, 2020; 5 Pages; Japanese Patent Office.

* cited by examiner

ILLUMINATED BANDAGE AND METHOD FOR DISINFECTING A WOUND

This application claims the benefit of priority under 35 U.S.C. § 119 of U.S. Provisional Application Ser. No. 61/908,919 filed on Nov. 26, 2013, the content of which is relied upon and incorporated herein by reference in its entirety.

BACKGROUND

This disclosure pertains to a light delivery system, and more particularly to an illuminated bandage for disinfecting a wound.

Band-aids or bandages typically include an anti-bacterial application or disinfect that is applied to a wound to kill bacteria or prevent infection to the wound. Bandages typically include an anti-bacterial treatment applied to the wound to decontaminate and clean the surface. The anti-bacterial treatment is typically applied to an absorptive material, such as cotton and held in contact with the wound via an adhesive or elastic wrap. It is desirable to provide a means for disinfecting a wound that does not rely solely on the application of an anti-bacterial lotion to the wound.

SUMMARY

In accordance with one embodiment, an illuminated bandage for disinfecting a wound is provided. The illuminated bandage includes a power source, a light source coupled to the power source to generate light and a patch. The patch includes a supporting medium and at least one light diffusing element disposed in the supporting medium and optically coupled to the light source. The light diffusing element outputs light to promote a photochemical reaction to disinfect a wound surface proximate thereto.

In accordance with another embodiment, a method of disinfecting a wound is provided comprising the steps of providing a patch having one or more light diffusing elements disposed in a supporting medium and applying the patch to a wound surface. The method also includes the steps of generating light having a wavelength for promoting photochemical reaction, and applying the light to the one or more light diffusing elements to promote a photochemical reaction to disinfect the wound surface.

Additional features and advantages will be set forth in the detailed description which follows, and in part will be readily apparent to those skilled in the art from that description or recognized by practicing the embodiments as described herein, including the detailed description which follows, the claims, as well as the appended drawings.

It is to be understood that both the foregoing general description and the following detailed description are merely exemplary, and are intended to provide an overview or framework to understanding the nature and character of the claims. The accompanying drawings are included to provide a further understanding, and are incorporated in and constitute a part of this specification. The drawings illustrate one or more embodiments, and together with the description serve to explain principles and operation of the various embodiments.

DETAILED DESCRIPTION

Figure 1:
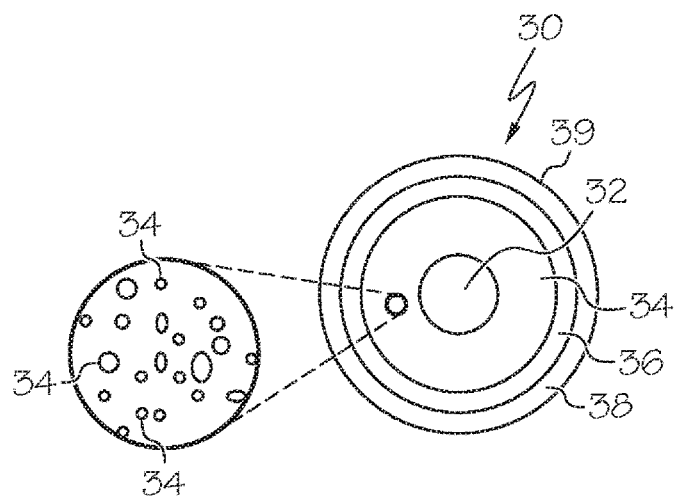
FIG. 1 is a diagrammatic cross-sectional view of one embodiment of a light diffusing fiber useful as a light diffusing element in an illuminated bandage.
Figure 2:
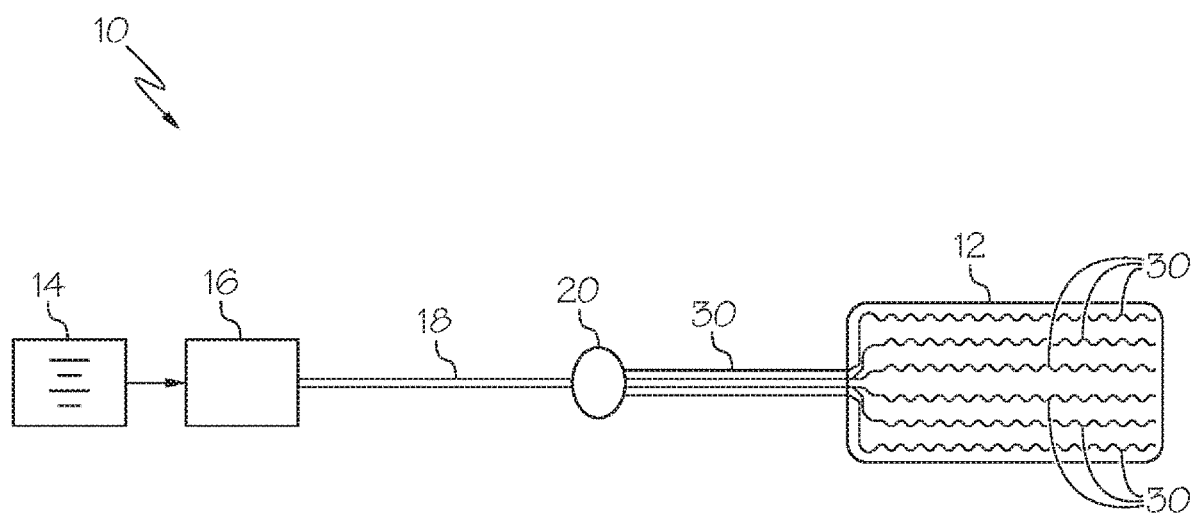
FIG. 2 is a top schematic diagram illustrating an illuminated bandage for disinfecting a wound with the use of the light diffusing element, according to one embodiment.

Reference will now be made in detail to the present preferred embodiments, examples of which are illustrated in the accompanying drawings. Whenever possible, the same reference numerals will be used throughout the drawings to refer to the same or like parts.

The following detailed description represents embodiments that are intended to provide an overview or framework for understanding the nature and character of the claims. The accompanied drawings are included to provide a further understanding of the claims and constitute a part of the specification. The drawings illustrate various embodiments, and together with the descriptions serve to explain the principles and operations of these embodiments as claimed.

Figure 3:
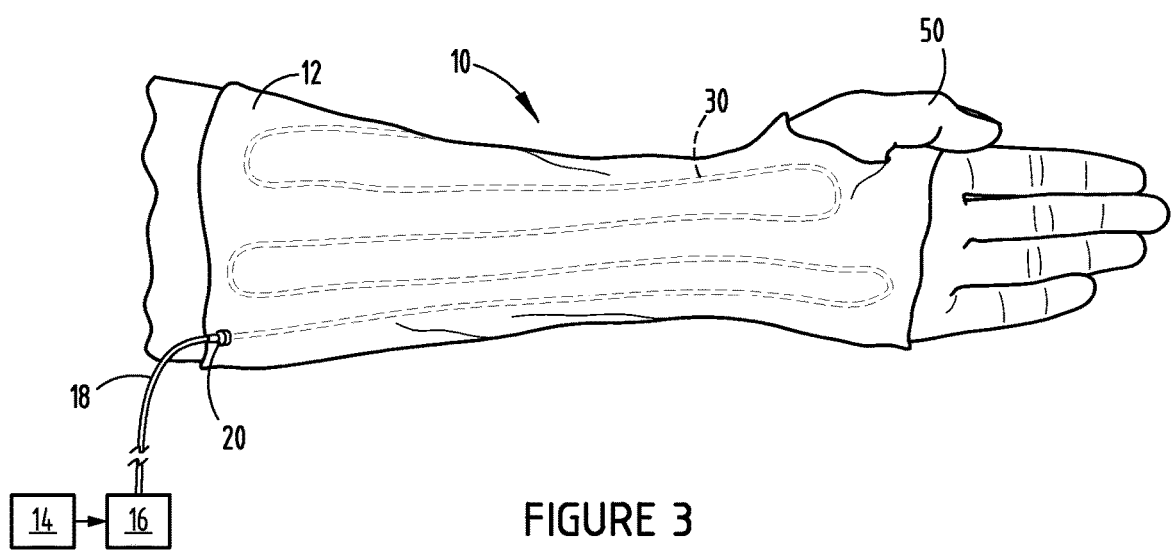
FIG. 3 is a perspective view of the bandage shown worn on the arm and hand of a person to cover and treat a wound.
Figure 4:
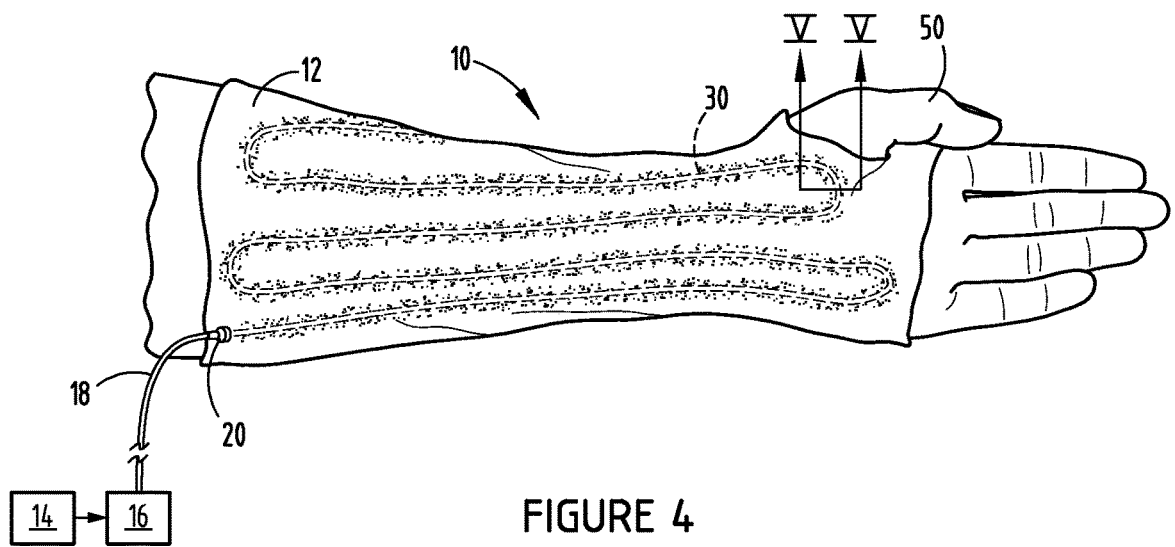
FIG. 4 is a perspective view of the illuminated bandage showing the light diffusing element illuminated to disinfect the wound.

Referring to FIGS. 1-5, an illuminated bandage 10 is illustrated for disinfecting a wound on a living being (e.g., person), such as a flesh wound on the surface of a hand and/or arm 50. The illuminated bandage 10 has a patch 12 configured to engage the surface proximate to a wound, such as the outer skin of a living being so as to cover the flesh wound in the skin. The patch 12 may include an elastic covering that covers the skin and wraps around the hand and/or arm as shown in FIGS. 3 and 4. In other embodiments, the patch 12 may include an adhesive for adhering to the skin. Other securing arrangements may be utilized to position the patch 12 proximate to the wound.

The illuminated bandage 10 employs an active light and an optional photocatalyst to promote a photochemical reaction in the volume on the surface of the hand and/or arm 50 to disinfect the hand and/or arm to treat the wound. The light applied to illuminate the wound may include light having a wavelength that serves to kill germs or inhibit the growth of microorganisms, such as bacteria. The light may be used alone or may be used in combination with a photocatalyst such as rutile $TiO_2$. The light wavelength may be in the range of 200 nm to 2000 nm, according to one embodiment. According to a specific embodiment, an ultraviolet (UV) light having a wavelength in the range of 200 to 400 nm may be used. The light may include a combination of wavelengths and may include a red laser light that is known to help increase sterility. Further, combinations of infrared (IR) light can also be used as an additional heat source for accelerating the photochemical processes.

The illuminated bandage 10 includes at least one electrically powered light source 16 for generating and supplying an active light with select wavelength(s) to promote the photochemical reaction. The light source 16 may be a collimated or Lambertian light source. The light source 16 may include one or more lasers, light emitting diodes (LEDs), incandescent bulbs, ultraviolet lamps or a combination of light sources. The light source(s) 16 may generate light having a unique color or may combine various colors, such as red, green and blue light sources to generate custom colors. In one embodiment, one or more ultraviolet light sources are employed.

Figure 5:
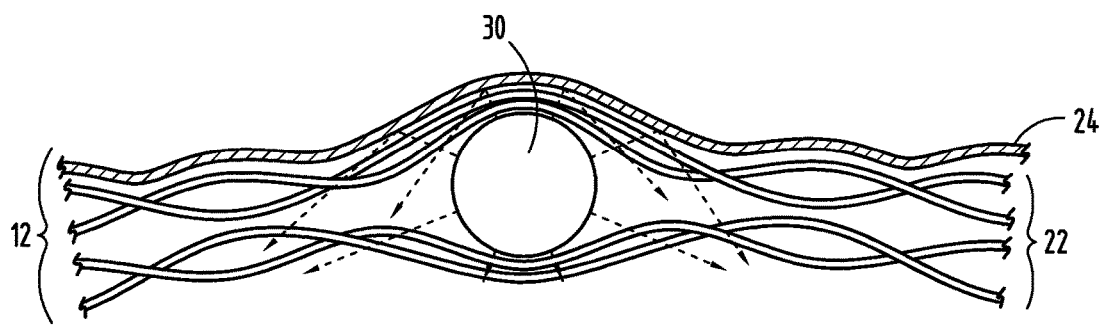
FIG. 5 is a cross-sectional view taken through line V-V of FIG. 4 further illustrating the light diffusing element disposed within a supporting medium of the bandage.

The illuminated bandage 10 also includes at least one light diffusing element 30 operatively coupled to the light source 16 to receive the light supplied by the light source 16 and disperses the light. The illuminated bandage 10 includes a patch 12 that includes a supporting medium 22 and the at least one light diffusing element 30. The light diffusing element 30 may be woven in the supporting medium 22 and optically coupled to the light source 16. The light diffusing element 30 outputs light to promote a photochemical reaction to disinfect the wound surface proximate thereto. The light diffusing element 30 is a high scatter light transmission element that receives the light generated by light source 16 and scatters and outputs the light to the wound surface to promote a photochemical reaction to disinfect the wound. The high scatter light transmission achieved with the light diffusing element 30 has a light attenuation of 0.5 dB/meter or greater. The light diffusing element 30 may include one or more light diffusing fibers according to one embodiment disposed within the supporting medium 22, such as is shown in FIG. 5. According to another embodiment, the light diffusing element 30 may include one or more light diffusing rods.

The powered light source 16 may be powered by a power supply 14 that supplies electrical power. The power supply 14 may include a portable battery supply, such as one or more batteries for providing electric current to the light source 16. The one or more batteries may be primary or secondary electrochemical cells. In other embodiments, the power supply may be a fixed power supply. The power source 14 and light source 16 may be located remote from the patch 12 or may be coupled to the patch 12.

The illuminated bandage 10 includes a supporting medium 22 which may include a woven material. The supporting medium 22 may include an absorptive material, such as cotton. The light diffusing element 30 is disposed within the woven supporting medium 22 and may be woven into the supporting medium 22. The light diffusing element 30 is able to produce light that substantially penetrates the supporting medium 22 particularly between the light diffusing element 30 and the wound. The patch 12 further includes an outer reflective layer 24 which has a reflective underlying surface that reflects light towards the wound proximate the underside of the bandage 10.

The illuminated bandage 10 may further include a low scatter light transmission medium 18 coupled between the light source 16 and the light diffusing element 30. According to one embodiment, the low scatter light transmission medium 18 may include an optical fiber designed to transmit light with low signal loss. The low scatter light transmission achieved with the transmission medium 18 has a light attenuation of less than 0.5 dB/meter. The low scatter light transmission medium 18 is shown in one embodiment coupled to the light diffusing element 30 by way of an optical coupler 20. It should be appreciated that the low scatter light transmission medium 18 may otherwise be operatively coupled to the light diffusing element 30 using various optical connections including splices, butt couplings and other light transmission couplings.

The low scatter light transmission medium 18 advantageously allows light generated by the light source 16 to be transmitted a substantial distance with low light signal loss to the patch 12 containing the light diffusing element 30. The low scatter light transmission medium 18 may be located in a separate room from the patch 12 which may be located in a clean room such that the light diffusing element 30 may be employed as a flexible remote light illuminator that allows continuous sterilization and wet, explosive or other sterile environments while positioning the light source 16 and power supply 14 outside of the clean room. As such, the light source 16 does not need to be sterilized and may be electrically powered from outside the clean room.

The low scatter light transmission medium 18 may include a transmission fiber that may be a single fiber, a bundled (or ribbonized) collection of fibers, a plastic optical fiber (POF), or other light transmission medium. The low scatter light transmission medium 18 may employ a fused silica rod, according to another embodiment, that can also be used as efficient delivery of light from the light source 16 to the light diffusing element 30. The low scatter transmission medium 18 may be connected to the light diffusing element 30 by the optical coupler 20 or by butt coupling to the light diffusing element 30.

The light diffusing element 30 may be configured as a single light diffusing fiber or may be bundled (or ribbonized) collections of light diffusing fibers. The light diffusing fiber may be flexible, thus allowing ease in installation within the patch 12. In one embodiment, the light diffusing fiber has a diameter of less than 1,000 microns, or more particularly of about 250 microns. In other embodiments, the light diffusing element may be more rigid such as in the form of a light diffusing rod having a diameter greater than 1,000 microns.

One embodiment of a light diffusing fiber 30 is illustrated having a typical cross-sectional structure shown in FIG. 1. The light diffusing fiber 30 may include the formation of random air lines or voids in one of the core and cladding of a silica fiber. Examples of techniques for designing and forming such light diffusing fibers may be found, for example, in U.S. Pat. Nos. 7,450,806; 7,930,904; and 7,505,660, and U.S. Patent Application Publication No. 2011/0305035, which are hereby incorporated by reference. The light diffusing element 30 has a glass core 32 which may include an F-doped core. An $SiO_2$ cladding layer 34 having air lines for scattering light is shown surrounding the core 32. The cladding layer 34 may be formed to include air lines or voids to scatter the light and direct the light through the side walls 39. It should be appreciated that the random air lines 34 may be disposed in the core 32 or in the cladding 36 or in both, according to various embodiments. It should be appreciated that high scattering losses are generally preferred in the light diffusing fiber 30. A low index polymer primary protective layer 36 generally surrounds the cladding layer 34. Additionally, an outer secondary layer 38 may be disposed on the primary protective layer 36. Primary protective layer 36 may be soft and liquidy, while secondary layer 38 may be harder.

The secondary layer 38 may include a photoreactive agent according to one embodiment. The photoreactive agent may be provided as the secondary coating having a hardness greater than the first cladding coating. The photoreactive agent may include materials such as $TiO_2$, $W_2O_3$, and other catalytic elements that photo-oxidizes when the light activates the material.

Scattering loss of the light diffusing fiber 30 may be controlled throughout steps of fiber manufacture and processing. During the air line formation process, the formation of a greater number of bubbles will generally create a larger amount of light scatter, and during the draw process the scattering can be controlled by using high or low tension to create higher or lower loss, respectively. To maximize loss of light, a polymeric cladding may be desirably removed as well, over at least a portion of the light diffusing fiber 30 length if not all. Uniform angular loss in both the direction of light propagation, as well as in the reverse direction can be made to occur by coating the light diffusing fiber 30 with inks that contain scattering pigments or molecules, such as $TiO_2$. An ultraviolet light source may be used as well, with a fluorescent dye or phosphor materials applied to the fiber cladding (effectively down converting the ultraviolet wavelength of light with approximately 100 percent efficiency to a desired wavelength). Use of such fluorescence downconversion creates very uniform angular light distribution. The high scattering light diffusing fiber 30 may have a modified cladding to promote scattering and uniformity. Intentionally introduced surface defects on the light diffusing fiber 30 or core or cladding may also be added to increase light output, if desired.

The light diffusing fiber 30 may have a region or area with a large number (greater than 50) of gas filled voids or other nano-sized structures, e.g., more than 50, more than 100, or more than 200 voids in the cross section of the fiber. The gas filled voids may contain, for example, $SO_2$, Kr, Ar, $CO_2$, $N_2$, $O_2$ or mixture thereof. The cross-sectional size (e.g., diameter) of the nano-size structures (e.g., voids) may vary from 10 nanometers to 1 micrometer (for example, 15 nanometers to 500 nanometers), and the length may vary depending on the area of the surface to be disinfected.

While the light diffusing element 30 is shown and described herein as a light diffusing fiber having air lines, it should be appreciated that other light scattering features may be employed. For example, high index materials such as $GeO_2$, $TiO_2$, $ZrO_2$, ZnO, and others may be employed to provide high scatter light transmission. It should further be appreciated the light diffusing element 30 may be a light diffusing rod that is less flexible, has a larger diameter and may have no coating.

A method of disinfecting a wound by promoting a photochemical reaction at the surface of the wound with the use of the illuminated bandage 10 will now be described. The method includes the step of providing a patch 12 having one or more light diffusing elements 30 woven into or otherwise disposed in a supporting medium 22. The patch 12 is applied to a wound surface. The method includes generating light having a wavelength for promoting photochemical reaction, and applying the light to the one or more light diffusing elements 30 to promote photochemical reaction to disinfect the wound.

The method may further include the step of delivering the light from a light source 16 to the light diffusing element 30 via a low scatter light transmission medium 18. The method may include providing electrical power from a battery 14 to power a light source to generate the light. The light diffusing element 30 may be a light diffusing fiber having a glass core, a cladding, and a plurality of light air lines disposed in one of the core and the cladding. At least one coating is disposed on the cladding, the at least one coating including a photoreactive agent. The light has at least one wavelength in the range of 200 nanometers and 2,000 nanometers, and may include ultraviolet light. The supporting medium 22 may include absorptive material. The patch 12 may include a plurality of light diffusing elements 30, wherein the light is applied to the plurality of light diffusing elements 30.

The illuminated bandage 10 may be used to disinfect an exposed wound in the flesh of the skin of a living being by applying the patch 12 to cover the skin including the wound area. This may be achieved with an elastic cover worn over the skin or wrapped around the skin. Alternatively, an adhesive may be used to adhere the patch to the skin. With the patch 12 applied to the skin, the light diffusing elements 30 generate light proximate to the wound to disinfect the wound. It should be appreciated that the illuminated bandage 10 could also be employed to disinfect an internal wound in which the patch is located internal to the body proximate to the wound.

Accordingly, the illuminated bandage 10 and method advantageously delivers light from a light source 16 coupled to a power source 14 to generate light to a light diffusing element 30 which outputs light to promote a photochemical reaction to disinfect a wound surface proximate thereto. The light diffusing element 30 is disposed in a supporting medium 22 of a patch 12 and optically coupled to the light source 16. As such, the illuminated bandage 10 disinfects a wound with the light in a manner that is safe, easy to use and clean.

Various modifications and alterations may be made to the examples within the scope of the claims, and aspects of the different examples may be combined in different ways to achieve further examples. Accordingly, the true scope of the claims is to be understood from the entirety of the present disclosure in view of, but not limited to, the embodiments described herein.

It will be apparent to those skilled in the art that various modifications and variations can be made without departing from the spirit or scope of the claims.

What is claimed is:

1. An illuminated bandage comprising:
   a power source;
   a light source coupled to the power source to generate light; and
   a patch comprising a supporting medium having an absorptive textile material and at least one light diffusing element disposed in the absorptive textile material of the supporting medium and optically coupled to the light source, wherein:
   the at least one light diffusing element comprises at least one light diffusing fiber;
   the at least one light diffusing fiber comprises a core, a cladding, and a plurality of air lines disposed in at least one of the core and the cladding; and
   the at least one light diffusing fiber outputs light through a sidewall of the light diffusing fiber to promote a photochemical reaction;
   wherein the at least one light diffusing fiber is woven into the absorptive textile material of the supporting medium.

2. The illuminated bandage of claim 1 further comprising a low scatter light transmission medium optically coupled between the light source and the at least one light diffusing fiber.

3. The illuminated bandage of claim 2 further comprising an optical coupler coupling the low scatter light transmission medium to the at least one light diffusing fiber.

4. The illuminated bandage of claim 1, wherein the power source comprises a battery.

5. The illuminated bandage of claim 1 further comprising at least one coating disposed on the cladding, the at least one coating comprising a photoreactive agent.

6. The illuminated bandage of claim 1, wherein the light source generates the light having at least one wavelength in the range between 200 nm and 2000 nm.

7. The illuminated bandage of claim 1, wherein the light source generates ultraviolet light.

8. The illuminated bandage of claim 1 further comprising a reflective surface for reflecting the light into the patch.

9. The illuminated bandage of claim 1, further comprising a fluorescent dye or phosphor material applied to the cladding to convert the light generated by the light source to the light outputted by the light diffusing fiber.

10. The illuminated bandage of claim 9, wherein the light generated by the light source and the light outputted by the light diffusing fiber have different peak wavelengths.

11. The illuminated bandage of claim 10, wherein the light generated by the light source is ultraviolet light having a wavelength in the range of 200 nm to 400 nm.

\* \* \* \* \*